United States Patent
Van Lint et al.

(10) Patent No.: US 9,943,536 B2
(45) Date of Patent: Apr. 17, 2018

(54) REACTIVATION OF HIV-1 GENE EXPRESSION TO TREAT PERSISTENT HIV INFECTION

(71) Applicant: UNIVERSITÉ LIBRE DE BRUXELLES, Brussels (BE)

(72) Inventors: Carine Van Lint, Brussels (BE); Olivier Rohr, Cestas (FR); Sophie Bouchat, Goutroux (BE); Jean-Stephane Gatot, Grand-Leez (BE)

(73) Assignee: UNIVERSITE LIBRE DE BRUXELLES, Bruxelles (BE)

( * ) Notice: Subject to any disclaimer, the term of this patent is extended or adjusted under 35 U.S.C. 154(b) by 0 days.

(21) Appl. No.: 14/348,820

(22) PCT Filed: Oct. 3, 2012

(86) PCT No.: PCT/EP2012/069544
§ 371 (c)(1),
(2) Date: Mar. 31, 2014

(87) PCT Pub. No.: WO2013/050422
PCT Pub. Date: Apr. 11, 2013

(65) Prior Publication Data
US 2015/0023907 A1    Jan. 22, 2015

Related U.S. Application Data

(60) Provisional application No. 61/542,545, filed on Oct. 3, 2011.

(51) Int. Cl.
| | | |
|---|---|---|
| *A61K 31/706* | (2006.01) | |
| *A61K 31/167* | (2006.01) | |
| *A61K 31/19* | (2006.01) | |
| *A61K 31/216* | (2006.01) | |
| *A61K 31/548* | (2006.01) | |
| *A61K 31/551* | (2006.01) | |
| *A61K 31/7068* | (2006.01) | |
| *A61K 45/06* | (2006.01) | |

(52) U.S. Cl.
CPC .......... *A61K 31/706* (2013.01); *A61K 31/167* (2013.01); *A61K 31/19* (2013.01); *A61K 31/216* (2013.01); *A61K 31/548* (2013.01); *A61K 31/551* (2013.01); *A61K 31/7068* (2013.01); *A61K 45/06* (2013.01)

(58) Field of Classification Search
CPC .... A61K 31/706; A61K 31/167; A61K 31/19; A61K 31/216; A61K 31/548; A61K 31/551; A61K 31/7068; A61K 45/06
See application file for complete search history.

(56) References Cited

FOREIGN PATENT DOCUMENTS

| WO | 02085400 A1 | 10/2002 |
| WO | 2006066775 A1 | 6/2006 |
| WO | 2008001391 A2 | 1/2008 |
| WO | 2009/032194 A1 | 3/2009 |
| WO | 2011038224 A1 | 3/2011 |
| WO | 2011113013 A2 | 9/2011 |

OTHER PUBLICATIONS

International Preliminary Report on Patentability for PCT application No. PCT/EP2012/069544, dated Apr. 8, 2014 (10 pages).
Laurence, Colin et al. 'Molecular Control of HIV-1 Postintegration latency: Implications for the Development of New Therapeutic Strategies'. Retrovirology. 2009, vol. 6, No. 11, pp. 1-29.
Zhu Wei Guo et al. 'Histone Deacetylase and DNA Methyltransferase Inhibitors Act Cooperatively to Reverse Transcriptional Silencing Induced by DNA Hypermethylation'. Proceedings of the American Association for Cancer Research Annual Meeting. 2000, No. 41, pp. 350.
Demonte, D et al. 'Administration of HDAC Inhibitors to Reactivate HIV-1 Expression in Latent Cellular Reservoirs: Implications for the Development of Therapeutic Strategies'. Biochemical Pharmacology. 2004, vol. 68, No. 4, pp. 1231-1238.
Imai, Kenichi et al. 'Involvement of Histone H3 Lysine (H3K9) Methyltranferase G9a in the Maintenance of HIV1 Latency and its Reactivation by BIX01294'. 2010, vol. 285, No. 22, pp. 16538-16545.
Friedman, Julia et al. 'Epigenetic Silencing of HIV-1 by the Histone H3 Lysine 27 Methyltranferase Enhancer of Zeste 2'. Journal of Virology. 2011, vol. 85, No. 17, pp. 9078-9089.
Hejnar, J et al. 'Reactivation of HIV-1 Latent Reservoir by an Inhibitor of H3K9me2 Methyltransferase G9a'. Epigenomics. 2010, vol. 2, No. 4, pp. 506-507.
International Search Report for PCT/EP2012/069544. Dated Feb. 15, 2013. 7 pages.
Cameron et al. (1999) "Synergy of demethylation and histone deacetylase inhibition in the re-expression of genes silenced in cancer," Nature Genetics. 21:103-107.
Victoriano et al. (2011) "Novel histone deacetylase inhibitor NCH-51 activates latent HIV-1 gene expression," FEBS Letters. 585:1103-1111.

*Primary Examiner* — Sahar Javanmard
(74) *Attorney, Agent, or Firm* — Lathrop Gage LLP; James H. Velema, Esq.

(57) ABSTRACT

The present invention provides new methods of treatment of lentiviral infections, more particularly to treat latent retroviral HIV infections, present in cells of the infected subject, based on the re-activation of said viruses. The invention uses a combination therapy using several agents that result in strong re-activation of the latent HIV-virus that could destroy the infected cells and elicite an immune response in the subject. This could present further spread of the infection, with the ultimate aim to eradicate the virus completely in said subject.

14 Claims, 10 Drawing Sheets

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gttagaccag atctgagcct                                              20

<210> SEQ ID NO 2
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gtgggttccc tagttagcca                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
actcgacaga ggagagcaag                                              20

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
gagaatctga ctgttctgat ga                                           22

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
gtcgacaacg gctccggc                                                18

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
ggtgtggtgc cagattttct                                              20
```

REACTIVATION OF HIV-1 GENE EXPRESSION TO TREAT PERSISTENT HIV INFECTION

RELATED APPLICATIONS

The present application is a 35 U.S.C. § 371 filing of International Application No. PCT/EP2012/069544, filed Oct. 3, 2012, which claims priority to U.S. Provisional Application No. 61/542,545, filed Oct. 3, 2011. The contents of each of the above-referenced applications are incorporated herein by reference in their entireties.

FIELD OF THE INVENTION

The present invention lies in the medical field, more particularly in the field of treating infectious diseases such as Human Immunodeficiency Virus (HIV). The invention provides a new method of treating (latent) HIV infections and compositions for use therein.

BACKGROUND OF THE INVENTION

Despite an efficient combination antiretroviral therapy (cART), the persistence of HIV-1 reservoirs, harboring transcriptionally silent but replication-competent stably integrated HIV-1 proviruses, seriously challenges the hope of HIV-1 eradication from cART-treated HIV-infected individuals. Indeed, the HIV-1 reservoirs are insensitive to cART and able to escape from the host immune response. Therefore, these latent reservoirs are a permanent source for virus reactivation and could be responsible for the rebound of plasma viral load observed after cART interruption. Consequently, cART treatment requires lifelong adherence, leading to several long term side effects and a life expectancy lower than that of uninfected individuals. Several therapeutic approaches aiming at achieving either a sterilizing cure (elimination of HIV from the human body) or—more likely—a functional cure (long-term control of HIV infection and disease progression in the absence of cART) have been proposed. In this context, reactivation of HIV-1 gene expression in latently-infected cells together with an efficient cART could serve as an adjuvant therapy aimed at decreasing the pool of persistent reservoirs.

HIV-1 transcriptional inhibition is crucial to the establishment and maintenance of post-integration latency. The chromatin organization and the epigenetic control of the HIV-1 promoter are key elements in this transcriptional silencing. On one hand, the repressive nucleosome nuc-1, located immediately downstream of the transcription start site, is maintained hypoacetylated by histone deacetylases (HDACs) in latent conditions. The laboratory of the inventors have previously reported that treatment of latently HIV-1-infected cell lines with HDAC inhibitors (HDACIs) induces viral transcription and remodeling of nuc-1. In addition, histone H3 lysine 9 (H3K9) methylation was shown by the laboratory of the inventors in microglial cells and by other in T cells or patient's cells to play a major role in chromatin-mediated repression of HIV-1 expression. The histone methyltransferases (HMTs) Suv39H1, which is primarily involved in H3K9 trimethylation (H3K9me3), and G9a, which is responsible for H3K9 dimethylation (H3K9me2), have been demonstrated to play a role in HIV-1 transcriptional silencing. On the other hand, the laboratory of the inventors and others have reported that DNA methylation is another epigenetic modification involved in HIV-1 postintegration latency. DNA methylation, probably together with repressive histone modifications, contributes to "lock" the silent state of the provirus and makes its return to an active state difficult. These observations suggest that HDAC or HMT or DNA methylation inhibitors together with efficient cART constitute good anti-latency drug candidates aimed at reducing/eliminating the pool of latent reservoirs to a level bearable by the host immune system.

In this context, several clinical studies have tested the reactivation potential of an HDACI alone (Valproic acid (VPA) or Vorinostat (suberoylanilide hydroxamic acid, SAHA), two FDA-approved drugs)) in ex-vivo cell cultures isolated from HIV+ patients blood. Whereas their published results or their unpublished preliminary results are encouraging, they question the efficiency of these drugs used alone to reduce the size of the latent HIV-1 reservoirs. The laboratory of the inventors have previously shown that the combined use of two drugs (an HDACI plus a NF-KappaB inducer, prostratin) causes a synergistic reactivation of HIV-1 production i.e. a higher reactivation than the sum of the reactivations produced by each drug individually in latently-infected used cell lines. Moreover, the same drug combination reactivates HIV-1 expression in $CD8^+$-depleted PBMCs cultures from cART-treated patients in a higher proportion of cells than observed with the drugs used alone. They have therefore demonstrated a proof-of-concept for the coadministration of two different types of therapeutically promising HIV-1 inducers together with efficient cART as a therapeutic perspective to decrease the pool of latent HIV-1 reservoirs. However, in 40% of their cultures, they could not detect any viral outgrowth following treatment with prostratin and HDACIs individually or in combination. This could result from a stronger epigenetic repression of some integrated proviruses in resting cells that would hinder an efficient viral transcriptional reactivation and expression, thereby highlighting the importance of finding new combinatory reactivation strategies. Consequently, the present invention uses the HIV-1 reactivation potential of two other classes of compounds, i.e. DNA methylation inhibitors and histone methyltransferase inhibitors (HMTIs), alone or in combination with other classes of HIV-1 inducers.

SUMMARY OF THE INVENTION

The present invention uses the HIV-1 reactivation potential of two classes of compounds, i.e. DNA methylation inhibitors (5-aza-2'deoxycitidine [5-aza-CdR or decitabine]) and histone methyltransferase inhibitors (chaetocin and BIX-01294), alone or in combination with other classes of HIV-1 inducers.

The present invention reports that a DNA methylation inhibitor or a HMT inhibitor alone or in combination with other HIV-1 inducers reactivates HIV-1 production from its latent state and to greater extend when the drugs are used in combination. Consequently, this could lead together with continuous antiretroviral therapy to a therapeutic strategy to decrease the pool of latent reservoirs in cART-treated HIV+ infected patients.

On one hand, the inventors have tested the reactivating effect of combinations including the DNA methylation inhibitor 5-aza-CdR, approved in human therapy for the myelodysplastic syndrome, and several HDACIs including different structural HDACI families used in human therapy (such as VPA, Sodium Butyrate (NaBut) or SAHA) or in clinical trial (such as MS-275) (FIG. 5). They have demonstrated that such combinations induced a synergistic reactivation of HIV-1 production in postintegration latency model T cell lines (at both the viral mRNA and protein levels) and that the best synergisms were observed using the combinations 5-aza-CdR+NaBut and 5-aza-CdR+SAHA (FIG. 5). These synergisms were due, at least partially, to the synergistic recruitment of unresponsive cells into the expressing cell population (FIG. 5b), and were accompanied by a partial demethylation of CpG dinucleotides in the HIV-1 5'LTR. Moreover, preliminary data from the inventors in CD8$^+$-depleted PBMCs cultures isolated from HIV$^+$ cART-treated patients with an undetectable viral load have highlighted that 5-aza-CdR may increase the reactivation potential of SAHA.

In a preferred embodiment, the DNA methylation inhibitor such as 5-aza-CdR is combined with HDACIs including different structural HDACI families used in human therapy such as VPA, Sodium Butyrate (NaBut) or SAHA. The combination with Sodium Butyrate is particularly preferred due to its lower toxicity and higher activity as compared to SAHA.

On the other hand, the inventors have evaluated the therapeutic potential of HMT inhibitors (chaetocin and BIX-01294, two specific inhibitors of Suv39H1 or of G9a, respectively) for their effect on reactivation of HIV-1 from latency. First, in latently-infected cell lines, the inventors demonstrated that the HMTI chaetocin alone increased HIV-1 gene expression and production (FIG. 1) and functioned synergistically with the non-tumor NF-κB inducer prostratin (FIG. 2). Second, the inventors have measured HIV-1 recovery in ex-vivo cultures of CD8$^+$-depleted PBMCs or of resting CD4$^+$ T cells isolated from 67 HIV$^+$ cART-treated patients with undetectable viral load after treatment with an HMTI alone or in combination with other HIV-1 inducers (in absence of IL-2 and of allogenic stimulation). They have demonstrated, for the first time, that chaetocin induced HIV-1 recovery in 50% of CD8$^+$-depleted PBMCs cultures (Table 2a) and in 86% of resting CD4$^+$ T-cell cultures (Table 2b) isolated from HIV-1$^+$ cART-treated patients, whereas BIX-01294 reactivated HIV-1 expression in 80% of resting CD4$^+$ T-cell cultures (Table 4) isolated from similar patients. Moreover, they have showed that combinatory treatments including one HMTI and either the HDACI SAHA, or the non-tumor-promoting NF-κB inducer prostratin had a higher reactivation potential than treatments with these compounds alone (FIGS. 3 and 4 and Table 3). In conclusion, the inventors have showed for the first time that HMTIs used alone or in combination with other HIV-1 inducers cause HIV-1 recovery in resting memory CD4$^+$ T cells from cART-treated patients. These results were published in AIDS in July 2012 (BOUCHAT et al., AIDS, 26(12), 1473-1482.PMID:22555163). Although chaetocin and BIX-01294 cannot be safely administered to humans, their results constitute a proof-of-concept for the use of HMTIs in strategies aimed at reducing the pool of HIV-1 latent reservoirs. Since HMTIs also represent promising compounds in anti-cancer therapies, other safer HMTIs should be synthesized soon and evaluated for their reactivation potential in HIV-1$^+$ cART-treated individuals.

These results suggest the administration of DNA methylation or HMT inhibitors alone or in combination with other HIV-1 inducers together with continuous cART as potential therapeutic strategies to reactivate HIV-1 from latency in infected patients.

The present invention thus provides:
1. A method for treating a disease or condition associated with a retrovirus in a subject in need of such treatment, comprising administering to said subject a therapeutically or prophylactically effective amount of:
a) a DNA methylation inhibitor and
b) a histone deacetylase inhibitor.
2. The method according to point 1, wherein the histone deacetylase inhibitor, is administered after the DNA methylation inhibitor has been administered.
3. The method according to point 1 or 2, wherein said DNA methylation inhibitor is selected from the two classes of DNA methylation inhibitors (non-nucleoside and nucleoside demethylating agents) including: 5-azacytidine (azacitidine), 5-aza-2'-deoxycytidine (5-aza-CdR, decitabine), 1-β-Darabinofuranosyl-5-azacytosine (fazarabine), dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.
4. The method according to any one of points 1 to 3, wherein said DNA methylation inhibitor is 5-aza-2'-deoxycytidine (5-aza-CdR, decitabine).
5. The method according to any one of points 1 to 4, wherein said histone deacetylase inhibitor is selected from the different families of HDACI (hydroxamates, cyclic peptides, aliphatic acids, and benzamides) including TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103.
6. The method according to any one of points 1 to 5, wherein said histone deacetylase is suberoylanilide hydroxamic acid (SAHA, Vorinostat) or sodium butyrate (NaBut).
7. The method according to any one of points 1 to 6, wherein the combination of 5-aza-2'-deoxycytidine+SAHA and 5-aza-2'-deoxycytidine+NaBut are used.
8. A method for treating a disease or condition associated with a retrovirus in a subject in need of such treatment, comprising administering to said subject a therapeutically or prophylactically effective amount of a histone methyltransferase inhibitor.
9. The method according to point 8, wherein said histone methyltransferase inhibitor is selected from the group comprising: chaetocin, UNC0224, diazepinyl-quinazolinamine, non-SAM (S-adenosylmethionine) analog-based HMTase inhibitor, BIX-01294, BIX-01338 (hydrate), and 2-Cyclohexyl-N-(1-isopropylpiperidin-4-yl)-6-methoxy-7-(3-(pyrrolidin-1-yl)propoxy) quinazolin-4-amine.
10. The method according to point 8 or 9, wherein said histone methyltransferase is chaetocin or BIX-01294.
11. The method according to any one of points 8 to 10, additionally comprising the administration of:
an HIV inducer such as:
a) a NF-kappa-B-inducer selected from the group comprising: PMA, prostratin, bryostatin and TNF-alpha, and/or
b) a histone deacetylase inhibitor selected from the different families (hydroxamates, cyclic peptides, aliphatic acids, and benzamides) including: TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103, and/or c) a DNA methylation inhibitor selected from the two classes (non-nucleoside and nucleoside demethylating agents) including: 5-azacytidine (azacitidine), 5-aza-2'-deoxycytidine (5-aza-CdR, decitabine), 1-β-Darabinofuranosyl-5-azacytosine (fazarabine) and dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.

12. The method according to any one of points 8 to 11, wherein the combination of chaetocin+prostratin and chaetocin+SAHA are used.

13. The method according to any one of points 8 to 11, wherein the combination of BIX-01294+SAHA is used.

14. The method according to any one of points 1 to 13, wherein said retrovirus is selected from the group consisting of: HIV-1, HIV-2, HTLV-1 and HTLV-2.

15. A pharmaceutical composition or formulation comprising:
a) a DNA methylation inhibitor,
b) a histone deacetylase inhibitor, and
c) one or more additional components, as without limitation one or more solvents and/or one or more pharmaceutically acceptable carriers, optionally for use in treating a disease or condition associated with a retrovirus in a subject in need of such treatment said pharmaceutical composition.

16. The pharmaceutical composition according to point 15, wherein said DNA methylation inhibitor is selected from the two classes (non-nucleoside and nucleoside DNA demethylating agents) comprising: 5-azacytidine (azacitidine), 5-aza-2'-deoxycytidine (5-aza-CdR, decitabine), 1-β-Darabinofuranosyl-5-azacytosine (fazarabine) and dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.

17. The pharmaceutical composition according to point 15, wherein said DNA methylation inhibitor is 5-aza-2'-deoxycytidine.

18. The pharmaceutical composition according to any one of points 15 to 17, wherein said histone deacetylase inhibitor is selected from the different families (hydroxamates, cyclic peptides, aliphatic acids, and benzamides) including: TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103.

19. The pharmaceutical composition according to any one of points 15 to 18, wherein said histone deacetylase inhibitor is SAHA or NaBut.

20. The pharmaceutical composition according to any one of points 15 to 19, wherein said DNA methylation inhibitor is 5-aza-2'-deoxycytidine and said histone deacetylase inhibitor is SAHA or NaBut.

21. A pharmaceutical composition or formulation comprising:
a) a histone methyltransferase inhibitor, and
b) one or more additional components, as without limitation one or more solvents and/or one or more pharmaceutically acceptable carriers, optionally for use in treating a disease or condition associated with a retrovirus in a subject in need of such treatment.

22. The pharmaceutical composition according to point 21, wherein said histone methyltransferase inhibitor is selected from the group comprising: chaetocin, UNC0224, diazepinyl-quinazolinamine, non-SAM (S-adenosylmethionine) analog-based HMTase inhibitor, BIX-01294, BIX-01338 (hydrate), and 2-Cyclohexyl-N-(1-isopropylpiperidin-4-yl)-6-methoxy-7-(3-(pyrrolidin-1-yl)propoxy)quinazolin-4-amine.

23. The pharmaceutical composition according to point 21 or 22, additionally comprising:
an HIV inducer such as:
a) a NF-kappa-B-inducer selected from the group comprising: PMA, prostratin, bryostatin and TNF-alpha, and/or
b) a histone deacetylase inhibitor selected from the different families (hydroxamates, cyclic peptides, aliphatic acids, and benzamides) including: TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103, and/or
c) a DNA methylation inhibitor selected from the two classes (non-nucleoside and nucleoside demethylating agents) comprising: 5-azacytidine (azacitidine), 5-aza-2'-deoxycytidine (5-aza-CdR, decitabine), 1-β-Darabinofuranosyl-5-azacytosine (fazarabine) and dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.

24. The pharmaceutical composition according to point 23, comprising the combination of chaetocin+prostratin or chaetocin+SAHA.

25. The pharmaceutical composition according to point 23, comprising the combination of BIX-01294 and SAHA.

26. A method for producing the compositions or formulation according to any of the previous points, comprising admixing the different components into a composition or formulation.

27. The composition according to any one of points 15 to 25, for use in treating a disease or condition associated with a retrovirus, preferably selected from the group consisting of: HIV-1, HIV-2, HTLV-1 and HTLV-2 preferably of latent infections.

28. The composition according to any one of points 15 to 25, for use in eradicating latent retroviral infections, and/or destroying retroviral reservoirs.

29. The composition according to any one of claims 15 to 25 for use in treating a disease or condition associated with a retrovirus, preferably selected from the group consisting of: HIV-1, HIV-2, HTLV-1 and HTLV-2, more preferably of latent infections, wherein the histone deacetylase inhibitor is administered after the DNA methylation inhibitor was administered.

BRIEF DESCRIPTION OF THE FIGURES

The present invention is illustrated by the following figures which are to be considered for illustrative purposes only and in no way limit the invention to the embodiments disclosed therein.

A. Results for HMTIs Alone or in Combination with HIV-1 Inducers

Table 1. Chaetocin induces HIV-1 recovery in a dose-dependent manner in CD8$^+$-depleted PBMCs isolated from HIV-1-infected cART-treated patients with undetectable viral load. Cultures of CD8$^+$-depleted PBMCs were mock-treated or treated with chaetocin (30, 60 or 90 nmol/l) or with the positive control. Six days after treatment, the concentration of viral RNA in culture supernatants was determined (in copies/ml; 'l' indicates below the threshold).

TABLE 1

| | CD8$^+$-depleted PBMCs | | | | |
| Patients | mock | chaetocin 30 nM | chaetocin 60 nM | chaetocin 90 nM | C+ |
| --- | --- | --- | --- | --- | --- |
| H1 | l | l | l | l | 467 |
| H2 | l | l | 222 | 1825 | 241 |
| H3 | l | 1139 | 452 | 354 | 6665 |
| H4 | l | l | 1924 | 2057 | 15394 |
| H5 | l | l | l | l | 219 |
| H6 | l | l | l | 2371 | 5053 |
| Reactivated patients | | 1 | 3 | 4 | 6 |

Figure 2:
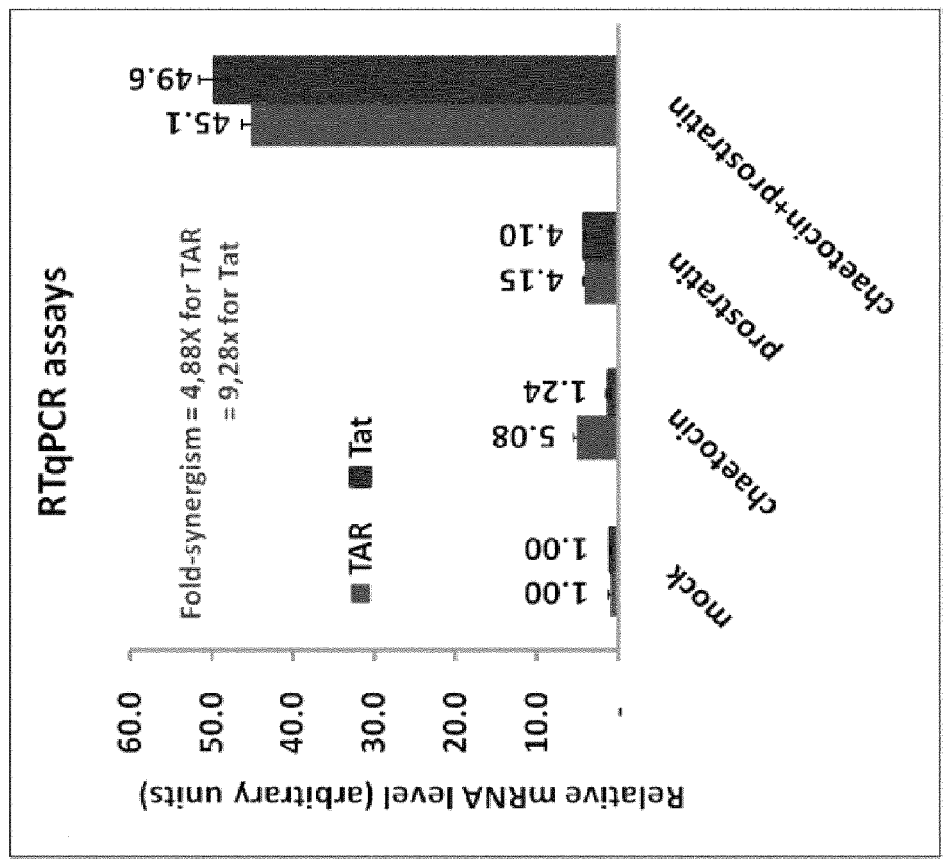

FIG. 2: The combined treatment chaetocin+prostratin synergistically increases HIV-1 transcription in the latently-infected J-Lat 15.4 cell line.

The J-Lat 15.4 cell line was mock-treated or treated as with chaetocin, prostratin or a combination of both drugs. Total RNA from these cells was extracted and reverse-transcribed using random primers. cDNAs were then used in a PCR reaction with primer pairs hybridizing either in TAR to quantify initiated transcripts or in Tat to quantify elongated transcripts. Results were normalized using β actin and are presented as histograms indicating the fold induction compared to mock-treated conditions.

Table 2: Chaetocin induces HIV-1 recovery in CD8$^+$-depleted PBMCs and in HLA DR$^-$ CD4$^+$ T cells from HIV-1-infected, cART-treated patients with undetectable viral load. (a) Cultures of CD8$^+$-depleted PBMCs were mock-treated or treated with chaetocin (90 nmol/l). Six days after treatment, the concentration of viral RNA in culture supernatants was determined. Total HIV-1 DNA is expressed as HIV-1 DNA copies/10$^6$ cells or as log HIV-1 DNA copies/10$^6$ cells ('/' indicates not-tested condition). (b) Limiting-dilution cultures of HLA DR$^-$ CD4$^+$ T cells were mock-treated or treated with chaetocin (45 or 90 nmol/l). The concentration of viral RNA in culture supernatants was determined. The last positive dilution culture indicates the presence of at least one cell carrying replication-competent and chaetocin-responsive virus.

TABLE 2

| | A: CD8$^+$-depleted PBMCs | | | | |
| Patients | mock | chaetocin | C$^+$ | HIV DNA (copies/10$^6$ cells) | Log HIV DNA |
| --- | --- | --- | --- | --- | --- |
| H1 | l | l | 467 | / | / |
| H2 | l | 1825 | 241 | / | / |
| H3 | l | 354 | 6665 | / | / |
| H4 | l | 2057 | 15394 | / | / |
| H5 | l | l | 219 | / | / |
| H6 | l | 2371 | 5053 | / | / |
| H7 | l | l | 306 | 1230 | 3.09 |
| H8 | l | l | 1480 | 2373 | 3.38 |
| H9 | l | 1566 | 1920 | 1366 | 3.14 |
| H10 | l | l | 8405 | 1527 | 3.18 |
| H11 | l | 797 | 19958 | 1110 | 3.05 |
| H12 | l | 477 | 4132 | 3309 | 3.52 |
| H13 | l | l | 272 | 2111 | 3.32 |
| H14 | l | 2388 | 387 | 2424 | 3.38 |
| H15 | l | l | 2691 | 995 | 3.00 |
| H16 | l | 467 | 7458 | 3465 | 3.54 |
| H17 | l | l | 2562 | 187 | 2.27 |
| H18 | l | l | 3695 | 3796 | 3.58 |
| Reactivated patients | 0 | 9 | 18 | | |
| % of reactivation | 0 | 50 | 100 | | |

TABLE 2-continued

| B: HLA DR⁻ CD4⁺ T cells | | | | | | | |
|---|---|---|---|---|---|---|---|
| Patients | mock | Dose of chaetocin | 1.5 × 10⁶ cells | 10⁶ cells | 5 × 10⁵ cells | 10⁵ cells | 5 × 10⁴ cells | C⁺ |

| Patients | mock | Dose of chaetocin | 1.5 × 10⁶ cells | 10⁶ cells | 5 × 10⁵ cells | 10⁵ cells | 5 × 10⁴ cells | C⁺ |
|---|---|---|---|---|---|---|---|---|
| P1 | I | 45 nM | / | 284 | 179 | I | / | 308 |
|    |   | 90 nM | / | I | 147 | I | / |     |
| P2 | I | 45 nM | / | / | 245 | 83 | I | 111 |
|    |   | 90 nM | / | / | I | I | I |     |
| P3 | I | 45 nM | / | I | I | I | / | 210 |
|    |   | 90 nM | / | I | I | I | / |     |
| P4 | I | 45 nM | / | I | 89 | I | / | 120 |
|    |   | 90 nM | / | / | 118 | 51 | I |     |
| P5 | I | 45 nM | / | 94 | I | I | / | 880 |
|    |   | 90 nM | / | 178 | 68 | 50 | 76 |     |
| P6 | I | 45 nM | 288 | 292 | 97 | I | / | 1451309 |
|    |   | 90 nM | 377 | 131 | 52 | 47 | I |     |
| P7 | I | 45 nM | 831 | 702 | 769 | 238 | I | 1021 |
|    |   | 90 nM | 1050 | 791 | 1043 | 359 | I |     |

TABLE 3

Patient's characteristics and reactivation status of ex-vivo cultures of patients cells.

| Cell types | Patients | Age | CD4⁺T count | Last treatment | Aviremic for (years) | mock | chaetocin | SAHA | chaetocin+ SAHA | prostratin | chaetocin+ prostratin | BIX-01294 | BIX-01294+ SAHA | C+ | HIV DNA copies/ 10⁶ cells |
|---|---|---|---|---|---|---|---|---|---|---|---|---|---|---|---|
| CD8⁺-depleted PBMCs | H1 | 38 | 962 | RTV + FAPV + AZT + 3TC | 4 | I | I | / | / | / | / | / | / | 467 | / |
| | H2 | 42 | 558 | AZT + ABC + 3TC | 9 | I | 1825 | / | / | / | / | / | / | 241 | / |
| | H3 | 53 | 786 | TDF + FTC + EFV | 5 | I | 354 | / | / | / | / | / | / | 6665 | / |
| | H4 | 46 | 680 | RTV + NVP + FAPV + ABC + 3TC | 7 | I | 2057 | / | / | / | / | / | / | 15394 | / |
| | H5 | 41 | 1239 | TDF + NVP + 3TC | 4 | I | I | / | / | / | / | / | / | 219 | / |
| | H6 | 69 | 1073 | TDF + RTV + ATV + 3TC | 5 | I | 2371 | / | / | / | / | / | / | 5053 | / |
| | H7 | 70 | 698 | TZV | 9 | I | I | / | / | / | / | / | / | 306 | 1230 |
| | H8 | 21 | 457 | 3TC, TDF, RTV, ATV | 3 | I | I | / | / | / | / | / | / | 1480 | 2373 |
| | H9 | 50 | 883 | TZV, LPV | 3 | I | 1566 | / | / | / | / | / | / | 1920 | 1366 |
| | H10 | 53 | 556 | 3TC + TDF + VNP | 4 | I | I | / | / | / | / | / | / | 8405 | 1527 |
| | H11 | 66 | 816 | TDF + KVX + NVP | 5 | I | 797 | / | / | / | / | / | / | 19958 | 1110 |
| | H12 | 61 | 536 | CBV + RTV + SQV | 5 | I | 477 | / | / | / | / | / | / | 4132 | 3309 |
| | H13 | 31 | 641 | 3TC + TDF + RTV + FAPV | 5 | I | I | / | / | / | / | / | / | 272 | 2111 |
| | H14 | 33 | 573 | 3TC + TDF + RTV + FAPV | 6 | I | 2388 | / | / | / | / | / | / | 387 | 2424 |
| | H15 | 58 | 557 | TRU + RTV + FAPV | 2 | I | I | / | / | / | / | / | / | 2691 | 995 |
| | H16 | 39 | 906 | KVX + NVP | 6 | I | 467 | / | / | / | / | / | / | 7458 | 3465 |
| | H17 | 48 | 690 | DDI + KVX + LPV | 4 | I | I | / | / | / | / | / | / | 2562 | 187 |
| | H18 | 69 | 570 | TRU + NVP | 2 | I | I | / | / | / | / | / | / | 3695 | 3796 |
| HLA DR⁻CD25⁻CD69⁻CD4⁺T cells | H19 | 36 | 693 | ATR | 1 | I | I | 624 | 444 | / | / | / | / | 256 | 1737 |
| | H20 | 44 | 481 | TRU + RTV + FAPV | 2 | I | 832 | 520 | 1204 | 612 | 564 | / | / | 4136 | 3037 |
| | H21 | 56 | 694 | ATR | 1 | I | 180 | 252 | 1428 | / | / | 665 | / | 524 | / |
| | H22 | 46 | 404 | TDF + FTC + NVP | 3 | I | 2780 | 2248 | 1868 | / | / | 1624 | / | 573312 | 4857 |
| | H23 | 45 | 481 | ATR | 2 | I | 1244 | 908 | 2796 | 1380 | 1440 | 1385 | / | 3208 | / |
| | H24 | 33 | 595 | ATR | 2 | I | 1616 | 952 | 1660 | 1064 | 1520 | 250 | / | 20436 | / |
| | H25 | 41 | 553 | KVX + ATV | 3 | I | 2000 | 336 | 3368 | / | / | 4292 | / | 968 | / |

TABLE 3-continued

Patient's characteristics and reactivation status of ex-vivo cultures of patients cells.

| Cell types | Patients | Age | CD4+T count | Last treatment | Aviremic for (years) | mock | chaetocin | SAHA | chaetocin+ SAHA | prostratin | chaetocin+ prostratin | BIX-01294 | BIX-01294+ SAHA | C+ | HIV DNA copies/ 10^6 cells |
|---|---|---|---|---|---|---|---|---|---|---|---|---|---|---|---|
| | H26 | 53 | 505 | TRU + RTV + FAPV | 2 | l | 680 | 540 | 994 | 2508 | 1628 | 412 | 1520 | 408 | 4047 |
| | H27 | 63 | 805 | TRU + NVP | 2 | l | l | l | l | l | l | l | l | 2040 | 670 |
| | H28 | 61 | 818 | KVX + EFV | 4 | l | 4944 | 1480 | 3632 | 2540 | 1392 | l | 6312 | 632 | 4643 |
| | H29 | 45 | 564 | TRU + RTV + FAPV | 2 | l | 300 | l | 200 | 3532 | 424 | / | / | 957136 | 1193 |
| | H30 | 55 | 401 | TRU + NVP | 1 | l | 328 | l | 668 | / | / | / | / | 2112 | 1373 |
| | H31 | 48 | 952 | TZV | 8 | l | l | 420 | l | 704 | l | / | / | 10180 | 1780 |
| | H32 | 53 | 424 | ATR | 1 | l | 2456 | 416 | 2668 | / | / | / | / | 105944 | 8197 |
| | H33 | 37 | 616 | TRU + KLT | 2 | l | 1000 | 412 | 872 | 420 | 1108 | 1780 | 1332 | 2308 | 2533 |
| | H34 | 48 | 821 | TRU + RTV + ATV | 1 | l | l | l | l | l | 892 | 1360 | l | 400 | 1363 |

Further to Table 3: Cultures of patient cells were mock-treated or treated with indicated compounds. Six days after treatment, the concentration of viral RNA in culture supernatants was determined (in copies/ml; l means below the threshold and '/' indicates an untested condition). Total HIV-1 DNA is expressed as HIV-1 DNA copies/$10^6$ cells or as log HIV-1 DNA copies/$10^6$ cells. The cultures indicated in gray showed a higher viral production with the combination of drugs than with the drugs alone, while the cultures indicated in black were reactivated only by the combinatory treatment and not by the drugs individually.

Figure 3:
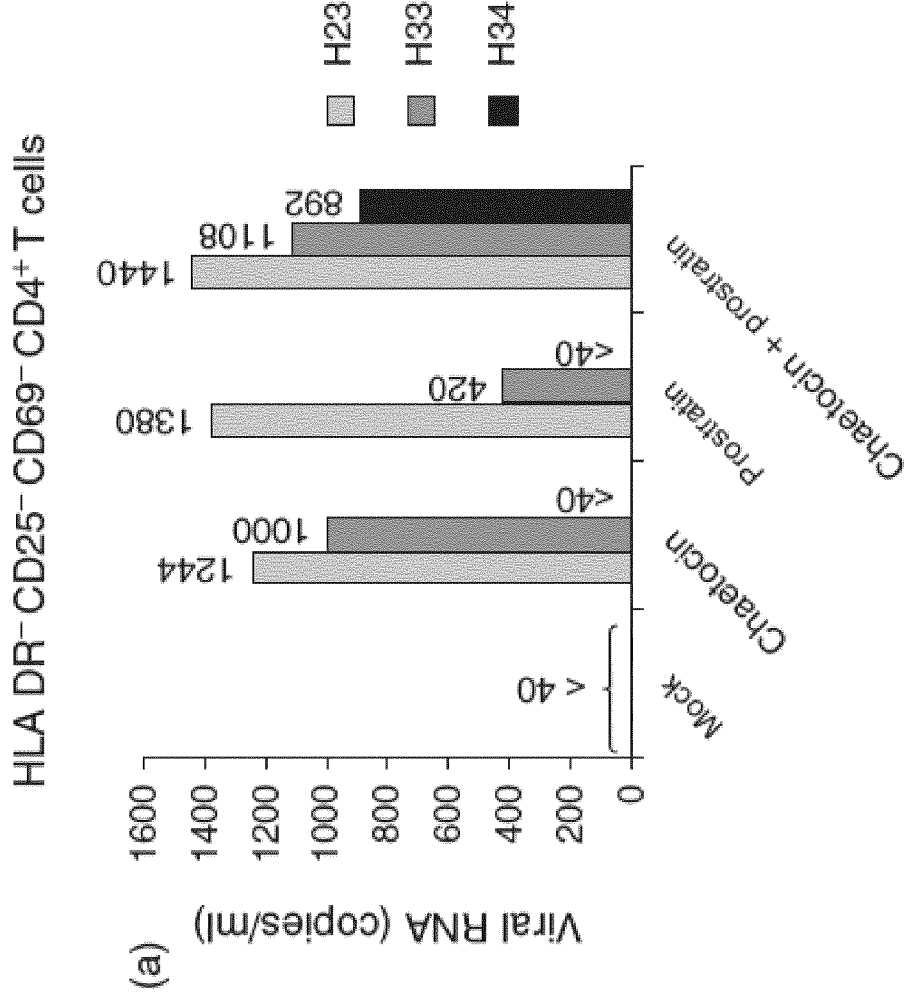
Figure 3:
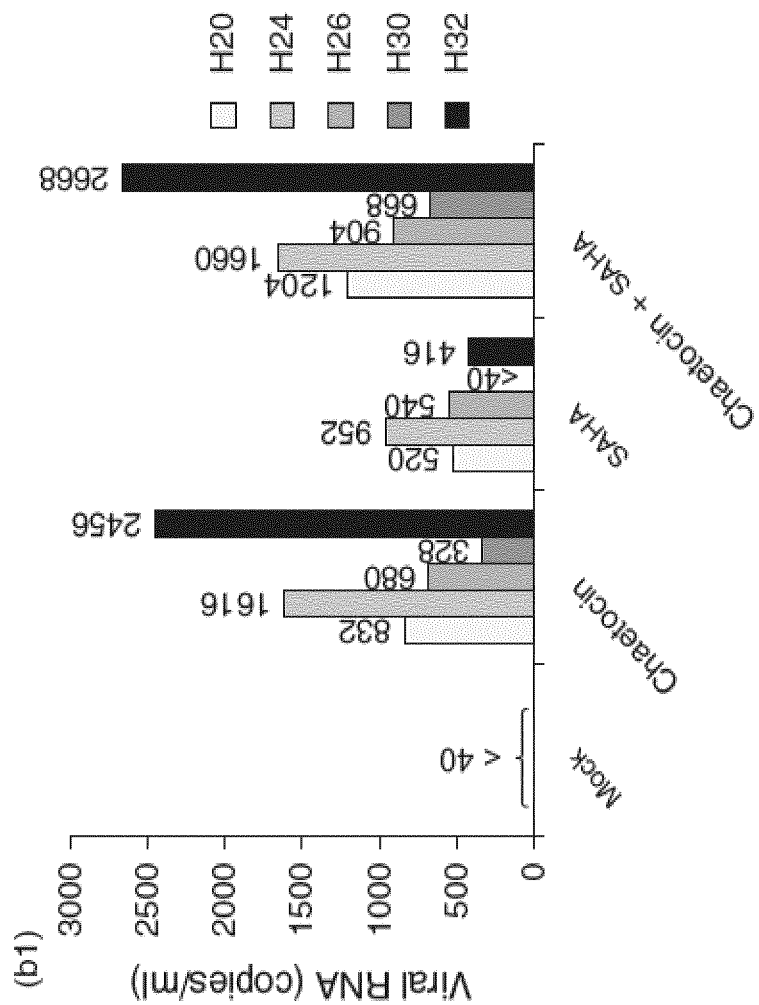
Figure 3:
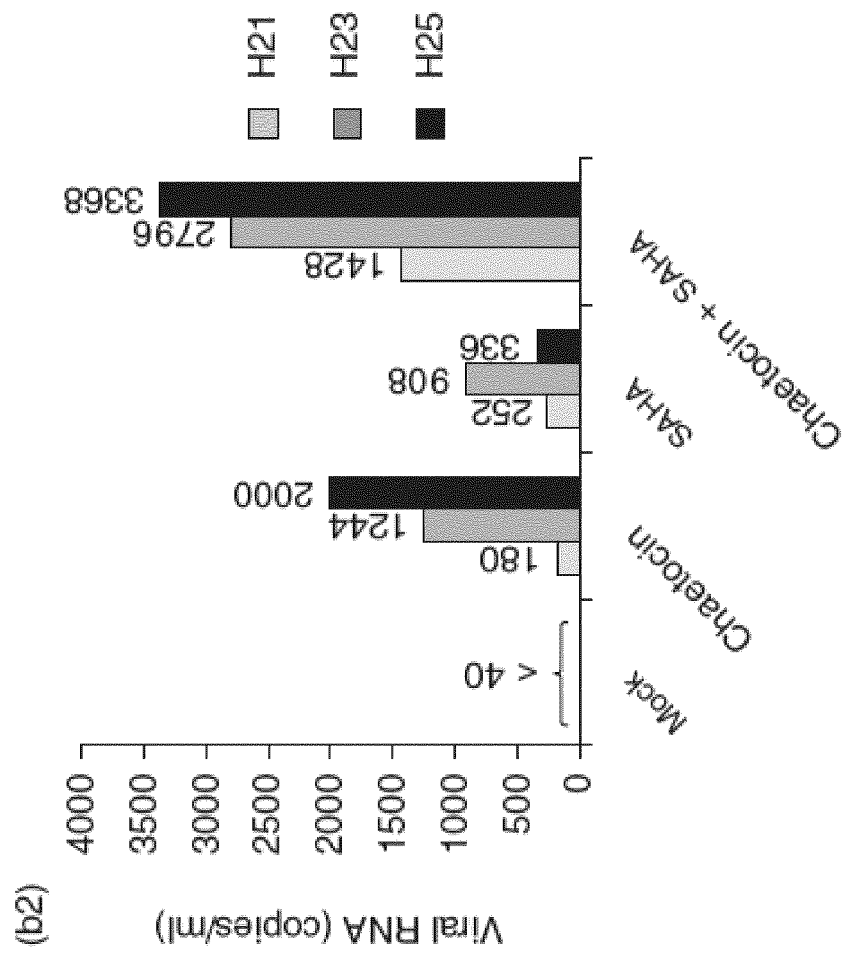

FIG. 3. The combinatory treatments including chaetocin induce a higher viral production in some ex-vivo cultures of resting memory CD4+ T cells from HIV-1-infected, cART-treated patients. Cultures of resting memory CD4+ T cells were mock-treated or treated as indicated. Six days after treatment, the concentration of viral RNA in culture supernatants was measured (in copies/ml). (a) The combination chaetocin+prostratin induces HIV-1 recovery in resting memory CD4+ T cells from HIV-1-infected, cART-treated patients. The reactivated patient cultures were classified in relevant categories where HIV-1 recovery after the combined treatment presented a higher viral production than after the individual treatment. (b) The combination chaetocin+SAHA induces HIV-1 recovery in resting memory CD4+ T cells from HIV-1-infected, cART-treated patients with undetectable viral load. The reactivated patient cultures were subdivided in two relevant categories: (b1) cultures in which HIV-1 recovery after the combined treatment was higher than after the individual treatments, (b2) and cultures in which a synergistic reactivation of viral RNA production was observed after the combined treatments.

Table 4. BIX-01294 alone induces HIV-1 recovery in resting memory CD4+ T cells from HIV-1-infected, cART-treated patients with undetectable viral load. Cultures of resting memory CD4+ T cells were mock-treated or treated with BIX-01294. Six days after treatment, the concentration of viral RNA in culture supernatants was determined in copies/ml (l indicates below the threshold).

TABLE 4

HLA DR− CD25− CD69− CD4+ T cells

| Patients | mock | BIX-01294 | C+ |
|---|---|---|---|
| H21 | I | 665 | 524 |
| H22 | I | 1624 | 573 312 |
| H23 | I | 1385 | 3 208 |
| H24 | I | 250 | 20 436 |
| H25 | I | 4292 | 968 |
| H26 | I | 412 | 408 |
| H27 | I | I | 2 040 |
| H28 | I | I | 632 |
| H33 | I | 1 780 | 2 308 |
| H34 | I | 1 360 | 400 |
| Reactivated patients | 0 | 8 | 10 |
| % of reactivation | 0 | 80 | 100 |

Figure 4:
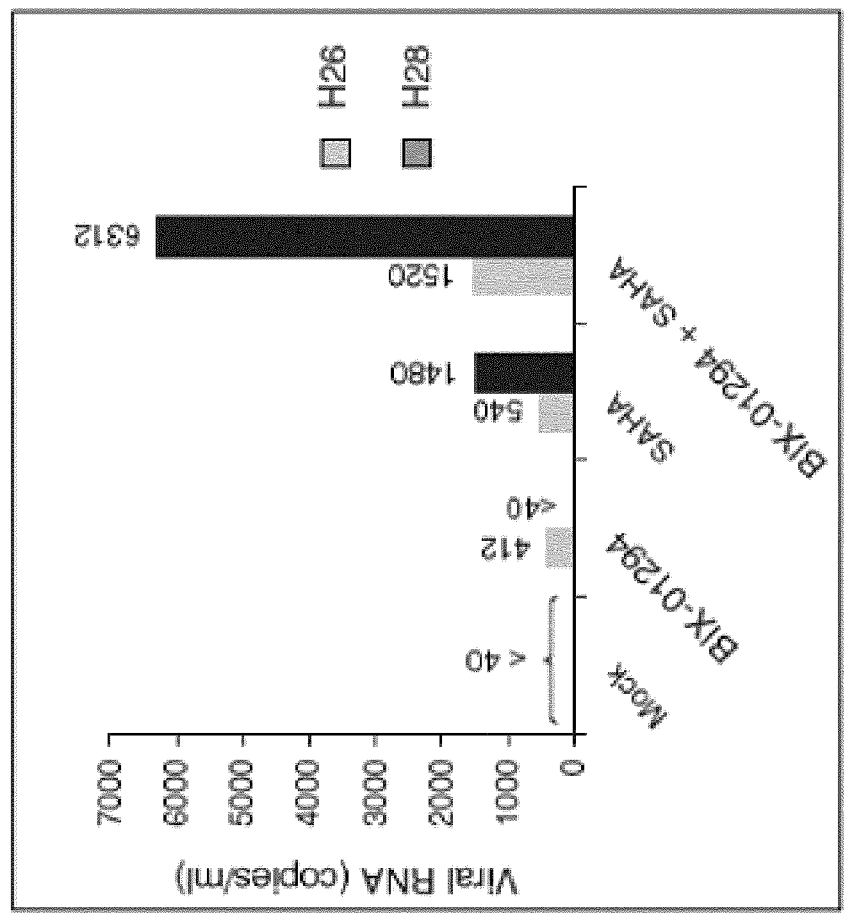

FIG. 4. BIX-01294 in combination with SAHA induces HIV-1 recovery in resting memory CD4+ T cells from HIV-1-infected, cART-treated patients with undetectable viral load. Cultures of resting memory CD4+ T cells were mock-treated or treated with BIX-01294 alone, with SAHA alone or with the combinationSAHA+BIX-01294. Six days after treatment, the concentration of viral RNA in culture supernatants was determined in copies/ml (I indicates below the threshold). A relevant category of patient cell cultures is shown in which we observed a synergistic increase in viral RNA copy number per milliliter after the combined treatment.

B. Results for DNA Methylation Inhibitors in Combination with HDACI

Figure 5:
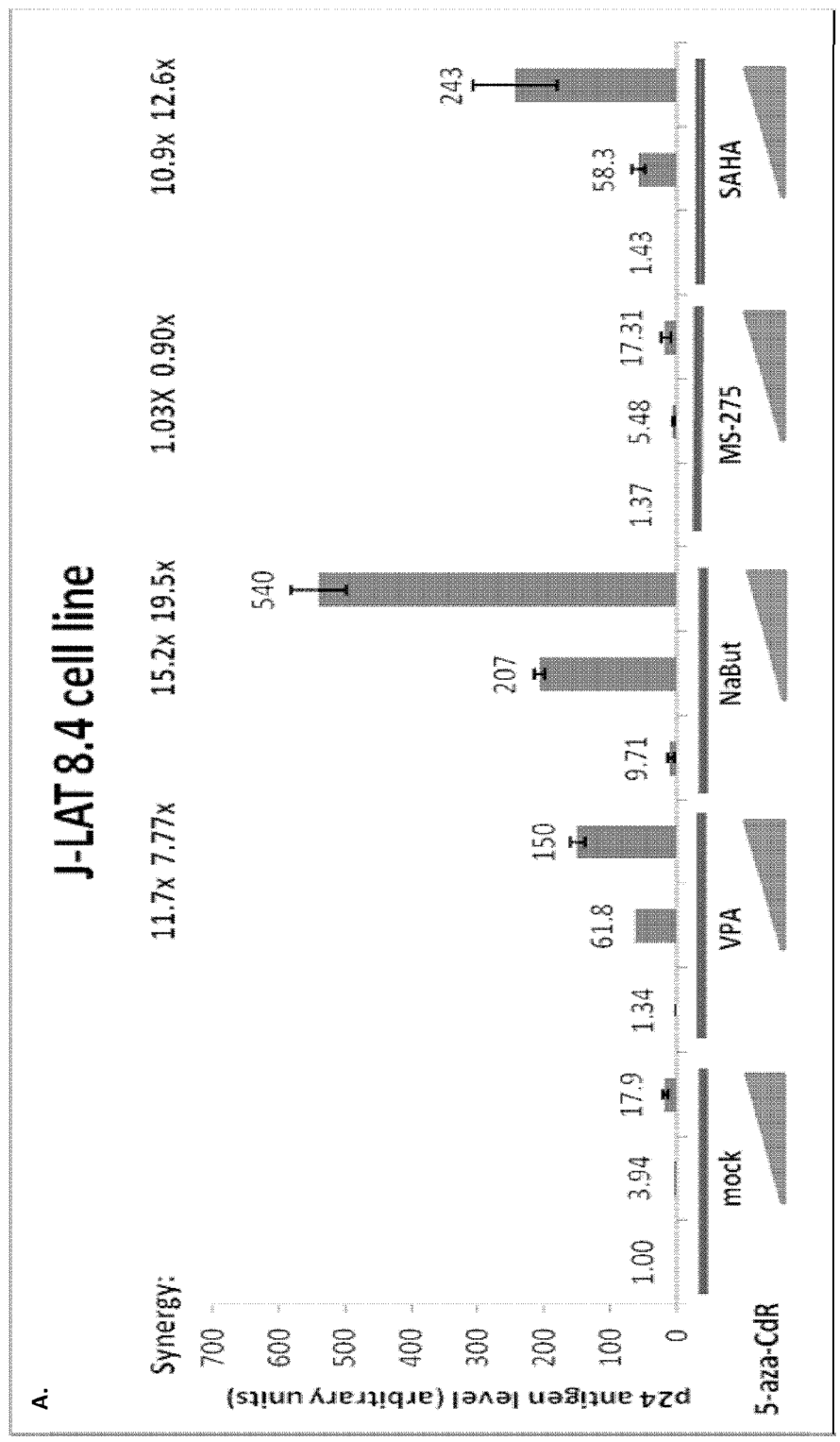
Figure 5:
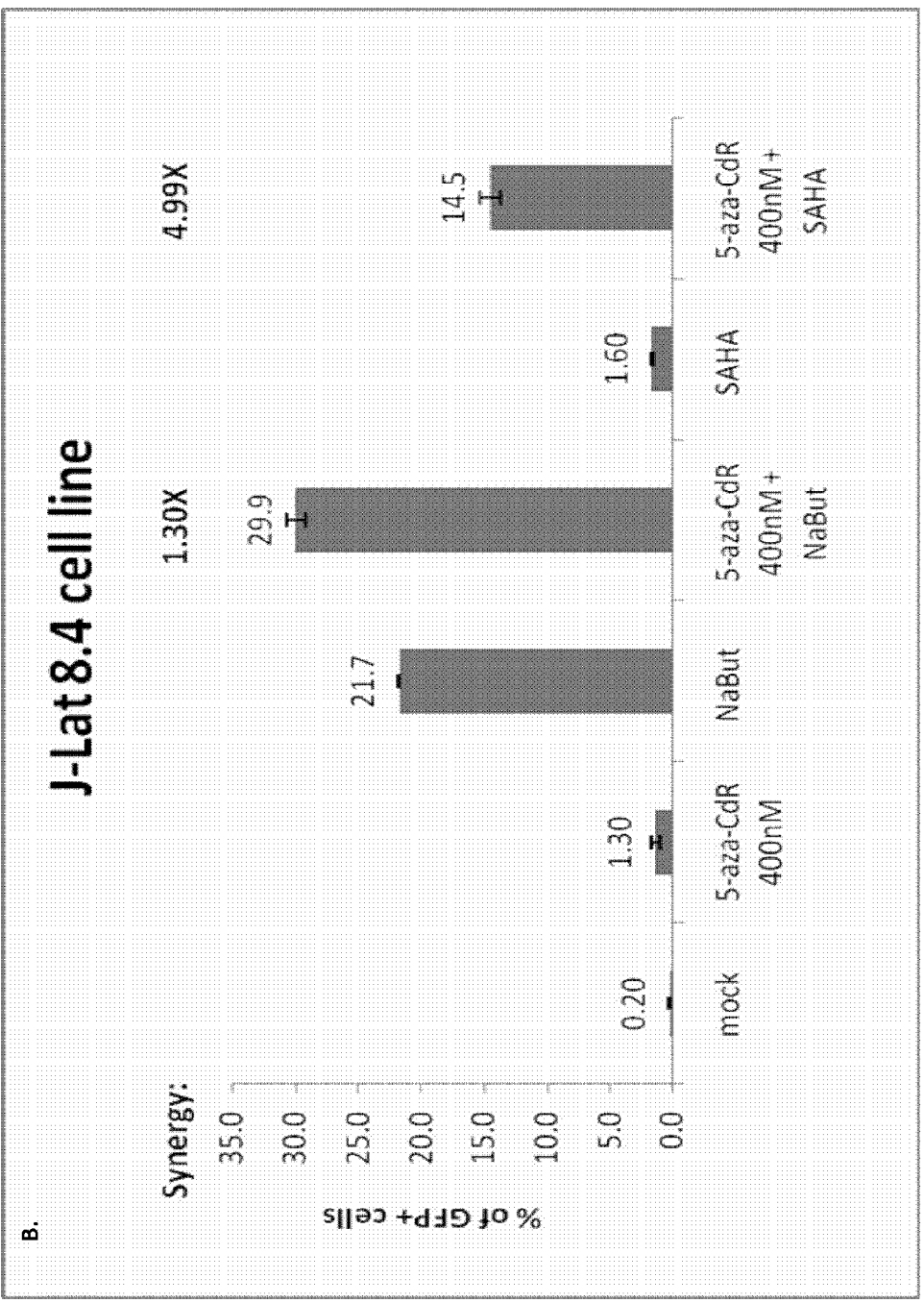
Figure 5:
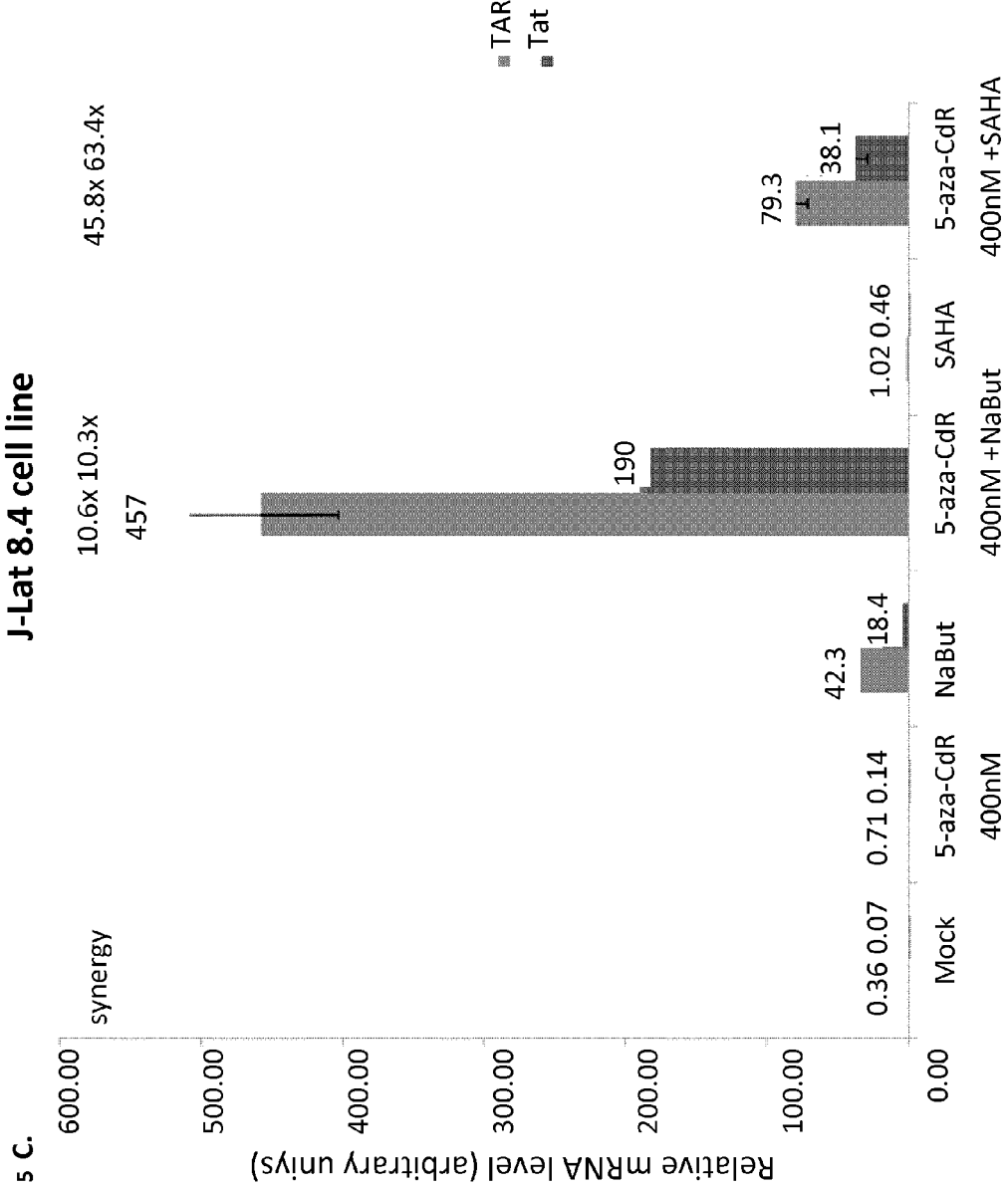

FIG. 5. Synergistic activation of HIV-1 expression by 5-aza-CdR and HDACI in J-Lat 8.4 cell line. J-Lat 8.4 cell line, which harbor a full-length latent HIV-1 provirus containing the gene coding for the green fluorescent protein GFP in place of nef, were mock-treated or treated with 5-aza-CdR for 48 hours. HDACIs were then added for 24 h. Means and standard errors of the means from duplicate samples are indicated. One representative experiment from three is represented A. At 72 h 5-aza-CdR post-treatment, p24 production in cell supernatant was measured. The result obtained with mock-treated cells was arbitrarily set at a value of 1. B. At 72 h 5-aza-CdR post-treatment, analyzes by FACS and representation of percentage of GPF+ cells in histograms. C. Total RNA from these cells was extracted and reverse-transcribed using random primers. cDNAs were then used in a PCR reaction with primer pairs hybridizing in TAR to quantify initiated transcripts and in the Tat gene to quantify elongated transcripts. Results were normalized using the β-actin gene primers. They are presented as histograms representing the fold induction compared to mock-treated conditions.

DETAILED DESCRIPTION OF THE INVENTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, term definitions may be included to better appreciate the teaching of the present invention.

For general methods relating to the invention, reference is made inter alia to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in 10 Molecular Biology and Short Protocols in Molecular Biology, 3rd Ed." (F. M. Ausubel et al., eds., 1987 & 1995); Recombinant DNA Methodology II (R. Wu ed., Academic Press 1995). General techniques in cell culture and media uses are outlined inter alia in Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991).

The term "retrovirus" is used herein in its conventional meaning and generally encompasses a class of viruses in which the genetic material is single-stranded RNA and which employ reverse transcriptase to transcribe the viral RNA into DNA in a host. Retroviruses as intended herein may particularly belong to the viral family Retroviridae, more particularly to the sub-family Lentivirinae. Retroviruses as intended herein may be pathogenic (i.e., causing a demonstrable disease phenotype in an infected host) or may be non-pathogenic (i.e., wherein an infected host's condition does not manifest a demonstrable disease phenotype). Particularly intended herein are retroviruses infecting animals, more preferably retroviruses of warm-blooded animals, even more preferably of vertebrate animals, still more preferably of mammals, yet more preferably of primates, and most preferably of humans. Particularly preferred herein are human retroviruses including without limitation HIV-1, HIV-2, HTLV-1 and HTLV-2.

Reference to "diseases or conditions associated with a retrovirus" generally encompasses any and all states of a host resultant from the host having been infected with the retrovirus. Without limitation, such states may be typified by the presence of viral biological material in the infected host, e.g., the presence of provirus in the genome of one or more cells of the infected host and/or the presence of viral nucleic acids, viral proteins or viral particles in the infected host. Without limitation, such states may comprise stages when the provirus is dormant or latent, pre-clinical stages when virus is produced in the infected host but without demonstrable disease symptoms, as well as clinical stages involving demonstrable disease symptoms, such as for example acquired immunodeficiency syndrome (AIDS) caused by HIV-1 and HIV-2, or adult T-cell leukaemia/lymphoma (ATLL) or tropical spastic paraparesis (TSP) caused by HTLV-1.

The Human Immunodeficiency Virus (HIV) is a Lentivirus, part of the family of Retroviridae. It is a single-stranded, positive-sense, diploid, enveloped RNA virus. Once entered in the target cell, the viral RNA genome of the virus is reverse transcribed into double-stranded DNA. This is done through a virally encoded reverse transcriptase that is transported along with the viral genome in the virus particle. After that, the transcribed viral DNA is imported into the cell nucleus and is integrated into the cellular DNA by an integrase (also virally encoded). The latency of the HIV and other lentiviruses is due to their ability to integrate in the host cell genome and stay in there in a latent form, i.e. without replicating. Due to this, the virus avoids detection by the immune system and can stay there for years resulting in a so called "reservoir" of HIV in the infected subject. Once the virus is re-activated, the viral DNA will be transcribed, producing new RNA genomes and viral proteins that are packaged and released from the cell as new virus particles, which can infect new cells. HIV mainly infects cells of the immune system, thereby weakening the immune response of the infected subject, which leads to its name "immunodeficiency virus". An HIV-positive subject may develop AIDS, or Acquired Immunodeficiency Syndrome, when the virus gets the ability to reproduce. In essence, the HIV will attach and destroy the CD4+ T-cells, macrophages, and microglial cells. The destruction of T-cells and macrophages will make the subject prone to all kinds of normally easy to avoid infections. When CD4+ T-cell numbers drop below the level of 200 cells/μL, the cell-mediated immunity is lost, and infections with a variety of opportunistic microbes appear and Common opportunistic infections and tumors, most of which are normally controlled by robust CD4+ T cell-mediated immunity then start to affect the patient. When a subject with HIV infection or AIDS is not treated, he can eventually die from otherwise easy to cure infections, due to the impairment of the immune system.

Due to the latent character of HIV, reservoirs of HIV-DNA can continue to exist during the whole life span of the infected subject, without any significant signs, if e.g. controlled by constant antiviral treatment. Stopping the treatment will however eventually result in re-activation of the virus. The infected subject can therefore never be fully freed of the HIV infection.

Two types of HIV have been characterized: HIV-1 and HIV-2. HIV-1 is the virus that was initially discovered and is the most virulent type, being more infective, [and the cause of the majority of HIV infections globally. HIV-2 is less infective and implies that fewer of those exposed to HIV-2 will be infected per exposure. HIV-2 is largely confined to West Africa.

As used herein, the term "agent" broadly refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, plants, fungi, or animal cells or tissues. Preferred though nonlimiting "agents" include nucleic acids, oligonucleotides, ribozymes, polypeptides or proteins, peptides, peptidomimetics, antibodies and fragments and derivatives thereof, aptamers, chemical substances, preferably organic molecules, more preferably small organic molecules, lipids, carbohydrates, polysaccharides, etc., and any combinations thereof.

The term "modulate" generally denotes a qualitative or quantitative alteration, change or variation specifically encompassing both increase (e.g., activation), or decrease (e.g., inhibition), of that which is being modulated. The term encompasses any extent of such modulation. For example, where modulation effects a determinable or measurable variable, then modulation may encompass an increase in the value of said variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation of the activity and/or level of intended target(s), i.e. the DNA methylation inhibitors and histone methyltransferases inhibitors as described herein may be specific or selective, i.e., the activity and/or level of intended target(s) may be modulated without substantially altering the activity and/or level of random, unrelated targets.

Reference to the "activity" of a target such as a complex or protein may generally encompass any one or more aspects of the biological activity of the target, such as without limitation any one or more aspects of its biochemical activity, enzymatic activity, signalling activity and/or structural activity, e.g., within a cell, tissue, organ or an organism. Preferably, said activity is a methylation activity.

In an embodiment, the activity of a target such as a complex or protein may be modulated and in particular reduced by introducing into or expressing in a cell, tissue, organ or an organism a dominant negative variant of said target, e.g., a dominant negative variant of one or more constituents of the complex, or a dominant negative variant of the protein.

Reference to the "level" of a target such as a complex or protein may preferably encompass the quantity and/or the availability (e.g., availability for performing its biological activity) of the target, e.g., within a cell, tissue, organ or an organism. For example, the level of a target may be modulated by modulating the target's expression and/or modulating the expressed target. Modulation of the target's expression may be achieved or observed, e.g., at the level of heterogeneous nuclear RNA (hnRNA), precursor mRNA (pre-mRNA), mRNA or cDNA encoding the target. By means of example and not limitation, decreasing the expression of a target may be achieved by methods known in the art, such as, e.g., by transfecting (e.g., by electroporation, lipofection, etc.) or transducing (e.g., using a viral vector) a cell, tissue, organ or organism with an antisense agent, such as, e.g., antisense DNA or RNA oligonucleotide, a construct encoding the antisense agent, or an RNA interference agent, such as siRNA or shRNA, or a ribozyme or vectors encoding such, etc. By means of example and not limitation, increasing the expression of a target may be achieved by methods known in the art, such as, e.g., by transfecting (e.g., by electroporation, lipofection, etc.) or transducing (e.g., using a viral vector) a cell, tissue, organ or organism with a recombinant nucleic acid which encodes said target under the control of regulatory sequences effecting suitable expression level in said cell, tissue, organ or organism. By means of example and not limitation, the level of the target may be modulated via alteration of the formation of the target (such as, e.g., folding, or interactions leading to formation of a complex), and/or the stability (e.g., the propensity of complex constituents to associate to a complex or disassociate from a complex), degradation or cellular localisation, etc. of the target.

The term "DNA methylation inhibitor" encompasses any known or yet unknown compound or agent that reduces, prevents, or removes methylation of DNA. There are several types of DNA methylation inhibitors known: 1) the "DNA methyltransferase inhibitors" or "DNMTi", encompassing compounds or agents that reduce the enzyme activity of the methyltransferase in any way, 2) "DNA demethylating agents", that remove methyl groups from the methylated DNA, and 3) "DNA-methylation inhibitors", that prevent the introduction of methyl groups into the DNA. Inhibitors of DNA methylation have been widely tested for the treatment of cancer and mostly are analogs of the nucleoside deoxycitidine. Several molecular variations of deoxycytidine have been developed, each modified at position 5 of the pyrimidine ring, as reviewed e.g. in "DNA methyltransferase inhibitors—state of the art", by J. Goffin & E. Eisenhauer (Annals of Oncology 13: 1699-1716, 2002). This distinctive feature is responsible for inhibiting DNMT. Analogs such as ara-C and gemcitabine, which do not possess this change in the pyrimidine ring, do not inhibit methylation. Exemplary oligodeoxynucleotides are those containing 5-azadeoxycytidine (AzadC), e.g. 5-azacytidine (azacitidine), 5-aza-2'-deoxycytidine (decitabine), 1-β-Darabinofuranosyl-5-azacytosine (fazarabine) and dihydro-5-azacytidine (DHAC); those containing 5-fluorodeoxycytidine (FdC); or those with oligodeoxynucleotide duplexes containing 2-H pyrimidinone, such as zebularine. An alternative mechanism for the inhibition of DNMT is the use of antisense oligodeoxynucleotides (ODNs). These are relatively short synthetic nucleic acids designed to hybridize to a specific mRNA sequence. The hybridization can block mRNA translation and cause mRNA degradation. Such antisense ODNs have been directed against DNMT mRNA and have caused a decrease in DNMT mRNA and protein. MG98 for example is an antisense oligodeoxynucleotide directed against the 3' untranslated region of DNMT1 mRNA. This agent has shown an ability to inhibit DNMT1 expression without effecting DNMT3. Effects may be synergistic in combination with decitabine. Alternatively, one could use non-nucleoside demethylating agents, such as, but not limited to: (−)-epigallocatechin-3-gallate, hydralazine, procaine and procainamide.

The term "histone methyltransferase inhibitor" or "HMTi" encompasses any known or yet unknown compound or agent that reduces the activity of histone methyltransferase in any way. Examples are: chaetocin, UNC0224 from Cayman Chemical; BIX-01294 from Tocris Bioscience; diazepinyl-quinazolinamine, non-SAM (S-adenosylmethionine) analog-based HMTase (histone methyltransferase) inhibitor from EMD Millipore; BIX 01294 from Enzo Life Sciences, Inc.; BIX-01338 (hydrate) from Sigma-Aldrich; UNC0638 (hydrate) (2-Cyclohexyl-N-(1-isopropylpiperidin-4-yl)-6-methoxy-7-(3-(pyrrolidin-1-yl)propoxy) quinazolin-4-amine) from Sigma-Aldrich, or any other compound.

The term "histone deacetylase inhibitor" or "HDACi" encompasses any known or yet unknown compound or agent that reduces the activity of histone deacetylases (HDACs). Examples are for example those compounds reviewed in Dokmanovic et al., 2007 (Mol Cancer Res Oct. 2007 5; 981). HDACi can be divided into several structural families including hydroxamates, cyclic peptides, aliphatic acids, and benzamides. Preferred examples are TSA, Vorinostat (SAHA), aminosuberoyl hydroxamic acids, M-Carboxycinnamic acid bishydroxamate, and derivatives including LAQ-824, LBH-589, and a sulfonamide derivative, belinostat (PXD-101), Panobinostat (LBH-589; Novartis AG) a cinnamic hydroxamic acid analogue of M-carboxycinnamic acid bishydroxamate, IF2357 (Italfarmaco SpA) is an HDACi that contains a hydroxamic acid moiety linked to an aromatic ring, aryloxyalkanoic acid hydroxamides; cyclic peptides such as the natural product depsipeptide (Romidepsin, FK-228, Gloucester Pharmaceutical Inc.), apicidin, and the cyclic hydroxamic acid-containing peptide group of molecules, FK-228 is a prodrug of an active agent, red FK, cyclic peptide mimic linked by an aliphatic chain to a hydroxamic acid, aliphatic acids, such as butyrate, phenylbutyrate, sodium butyrate and valproic acid, AN-9 (pivaloyloxymethyl butyrate from Titan Pharmaceutical, Inc.) is a prodrug of butyric acid, 5 NOX-275 (MS-275; Syndax Pharmaceutical Inc.) is a synthetic benzamide derivative, MGCD0103 (Methylgene Inc. Pharmion Corp.) is dihydrobromide salt of a substituted 2-aminophenyl benzamide. A preferred example is suberoylanilide hydroxamic acid (SAHA or vorinostat).

The term "NF-kappa-B inducers" encompasses all know or yet unknown compounds or agents that can induce or activate NF-kappa-B activity. Preferred examples are Prostratin (12-deoxyphorbol 13-acetate), phorbol myristate acetate (PMA), or Tumour Necrosis Factor alpha (TNF-alpha).

The present invention is further illustrated by the following examples, which do not limit the scope of the invention in any way.

The various active substances or agents of the present disclosure, such as histone methyltransferase inhibitors, histone desacetylase inhibitors and/or DNA methylation inhibitors, or NF-kappa-B inducers, inter alia complexes, proteins, nucleic acids, vectors, cells and agents as taught herein or pharmaceutically acceptable derivatives thereof, may be formulated into pharmaceutical compositions or formulations with one or more pharmaceutically acceptable carriers/excipients.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions of the invention may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions of the invention can be, for example, systemic, local, tissue-specific, etc., depending of the specific needs of a given application of the invention.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be is suitably accomplished by uniformly and intimately blending together a suitable amount of the active compound in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the active ingredient with a solid carrier such as described above to provide a mixture having the necessary compression properties, and then compacting the mixture in a suitable machine to the shape and size desired. Moulded tablets maybe made by moulding in a suitable machine, a mixture of powdered compound moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metereddose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The compounds and pharmaceutically acceptable salts thereof of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 15 1:10, more typically from about 5:1 to about 1:5, however any effective amount of surfactant may be used in an aqueous formulation to best suit the specific objectives of interest.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive.

Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The present active substances may be used alone or in combination with any anti-retroviral therapies (cART) known in the art ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order. Exemplary anti-retroviral drugs in combination therapy with which the present active substances may be employed include, without limitation, nucleoside and nucleotide reverse transcriptase inhibitors, non-nucleoside reverse transcriptase inhibitors, protease inhibitors, integrase inhibitors, entry inhibitors, maturation inhibitors and broad spectrum inhibitors. The dosage or amount of the present active substances used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 µg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of 20 body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every two or three weeks.

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred patients are human subjects.

As used herein, a phrase such as "a subject in need of treatment" includes subjects that would benefit from treatment of a given condition, particularly of a retroviral infection. Such subjects may include, without limitation, those that have been diagnosed with said condition, those prone to contract or develop said condition and/or those in whom said condition is to be prevented.

The terms "treat" or "treatment" encompass both the therapeutic treatment of an already developed disease or condition, such as the therapy of an already developed retroviral infection, as well as prophylactic or preventative measures, wherein the aim is to prevent or lessen the chances of incidence of an undesired affliction, such as to prevent the chances of contraction and progression of a retroviral infection. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment. In a preferred embodiment, "treatment" in the light of the present invention implies eradication of latent HIV infected "reservoirs", with the aim to free the patient from HIV infection.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present compounds.

EXAMPLES

Methods p24 ELISA assays, RT-qPCR and FACS were performed using standard methodologies. The reactivation tests were carried out in cultures of $CD8^+$-depleted PBMCs or HLA DR-cultures isolated from blood of $HIV-1^+$ cART-treated individuals with undetectable viral load (HIV-1 outgrowth was assessed with the Roche Amplicor kit and Abbott HIV-1 Realtime).

Example 1

Figure 1:
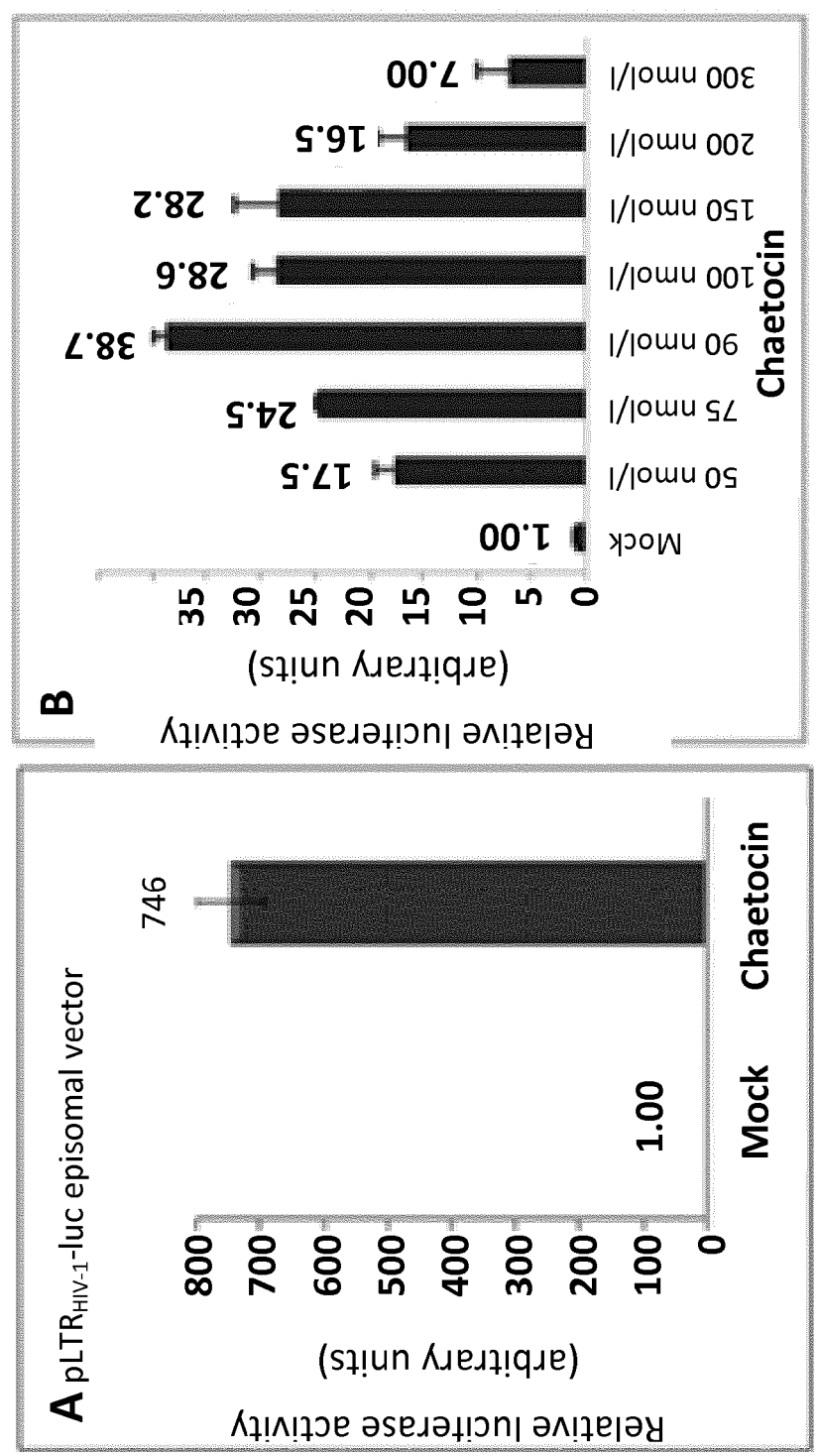
FIG. 1. Chaetocin induces HIV-1 recovery in a dose-dependent manner. (a, b) Chaetocin increases the transcriptional activity of the HIV-1 5'LTR in transfected T lymphoid cells. The Jurkat or SupT1 cell lines were transiently transfected with the PLTR$_{HIV-1}$-luc episomal reporter construct. At 24-h posttransfection, cells were mock-treated or treated with chaetocin as indicated. At 24-h postinduction, cells were lysed and assayed for luciferase activity. Luciferase activities were normalized with respect to protein concentrations. The result obtained with the mock-treated cells was arbitrarily set at a value of 1. (c, d) Chaetocin increases HIV-1 production in the latently infected J-Lat 15.4 cell line. The J-Lat 15.4 cell line was mock-treated or treated with chaetocin as indicated. p24 production in cell supernatants (c) or cellular viability (d) were measured. The result obtained with mock-treated cells was arbitrarily set at a value of 1 or 100%, respectively.
Figure 1:
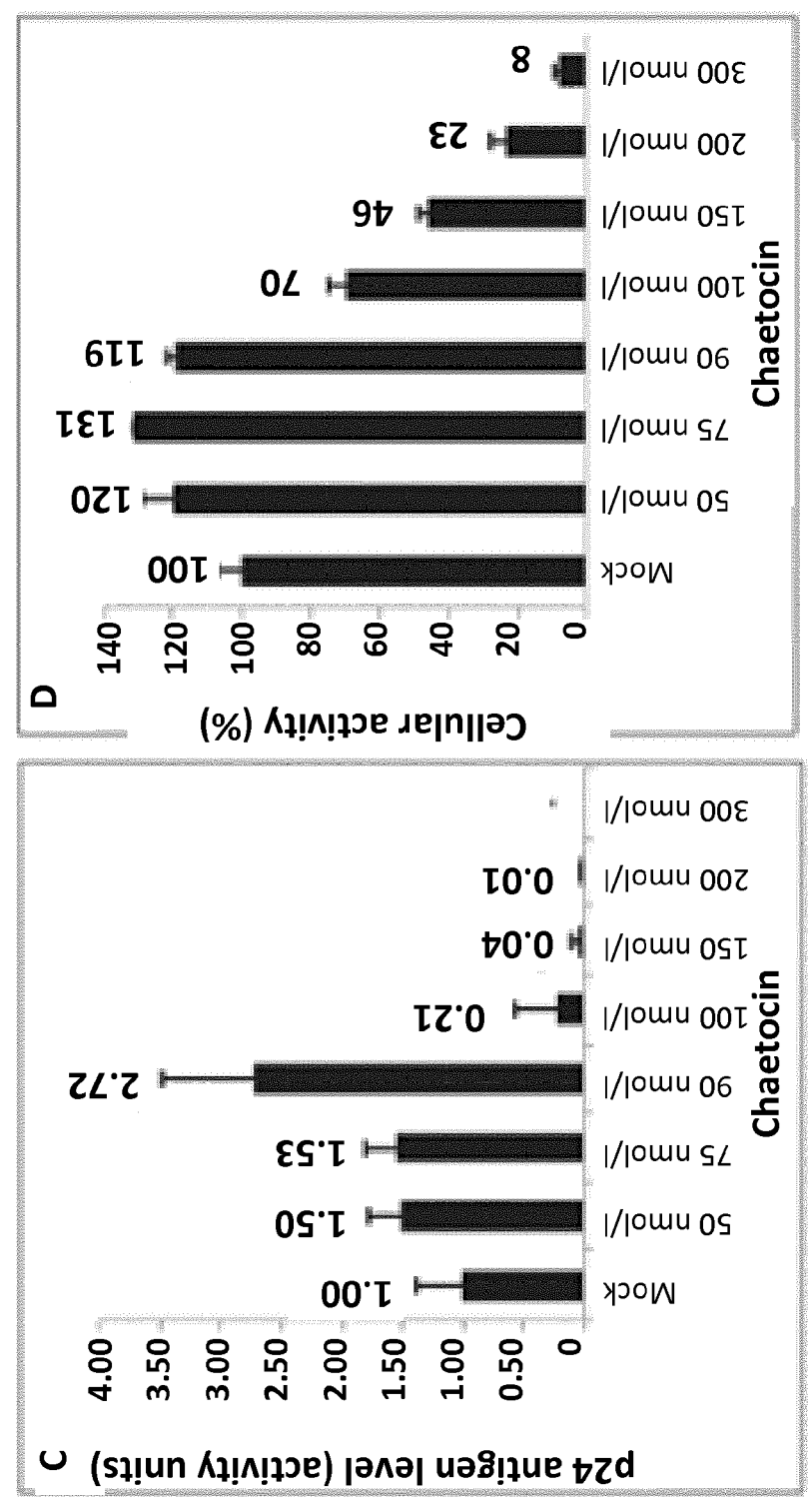

Effect of the Histone Methyltransferase Inhibitor Chaetocin on HIV-1 Gene Expression In this experiment, the inventors show that chaetocin, a histone methyltransferase inhibitor increases the transcriptional activity of the HIV-1 5'LTR in transfected T lymphoid cell lines. The Jurkat and SupT1 cell lines were transiently transfected with the $pLTR_{HIV-1}$-luc episomal vector reporter construct. At 24 h posttransfection, transfected cells were mock-treated or treated with chaetocin. Cells were lysed and assayed for luciferase activity. Luciferase activities were normalized with respect to protein concentration. The result obtained with mock-treated cells was arbitrarily set at a value of 1. The results are depicted in FIGS. 1(A and B), showing a clear increase of the luciferase activity in chaetocin-treated cells versus mock-treated cells.

In addition, the inventors tested the chaetocin effect in the latently-infected J-Lat 15.4 lymphoid T cell line and show that chaetocin increases HIV-1 production. The J-Lat 15.4 cell line was mock-treated or treated with chaetocin. HIV-1 p24 protein production in cell supernatants was measured. The result obtained with mock-treated cells was arbitrarily set at a value of 1. The results are depicted in FIG. 1(C) and clearly show an increase in p24 formation when the latently-infected lymphoid T-cells are treated with chaetocin.

FIG. 2 shows the increased HIV-1 transcription in the latently-infected J-Lat 15.4 cell line, when treated with chaetocin. The J-Lat 15.4 cell line was mock-treated or treated with chaetocin. Chaetocin treatment clearly activates HIV-1-RNA transcription. Total HIV-1-RNA was quantified as follows: Total RNA from these cells was extracted and reverse-transcribed using random primers. cDNAs were then used in a PCR reaction with primer pairs hybridizing either in TAR (FW, 5'-GTTAGACCAGATCTGAGCCT-3' (SEQ ID NO: 1) and RV, 5'-GTGGGTTCCCTAGT-TAGCCA-3') (SEQ ID NO: 2) to quantify initiated transcripts or in Tat (FW, 5'-ACTCGACAGAGGAGAGCAAG-3' (SEQ ID NO: 3) and RV, 5'-GAGAATCTGACTGTTCTGATGA-3') (SEQ ID NO: 4) to quantify elongated transcripts. Results were normalized using β actin gene primers (FW, 5'-GTCGACAACGGCTC-CGGC-3' (SEQ ID NO: 5) and RV, 5'-GGTGTGGTGCCA- GATTTTCT-3') (SEQ ID NO: 6) and are presented as histograms indicating the fold induction compared to mock-treated conditions.

Example 2

Chaetocin Induces HIV-1 Recovery in $CD8^+$-depleted PBMCs and in HLA $DR^-$ $CD4^+$ T Cells from cART-treated HIV-1 Positive Individuals with Undetectable Viral Load Cultures comprising $6.10^6$ $CD8^+$-depleted PBMCs were mock-treated or treated with chaetocin. Six days after treatment, the concentration of viral RNA in culture supernatants was determined by the Amplicor method (Roche Diagnostics). The results are depicted in Table 1 and 2A. The percentage of reactivation was calculated on all patients reactivated. Nine out of the eighteen tested PBMC cultures reactivated HIV-1 expression in response to chaetocin treatment, while none of them did when mock-treated. Subsequently, limiting-dilution cultures of HLA $DR^-$ $CD4^+$ T cells were performed and these cultures were mock-treated or treated with chaetocin. The last positive dilution culture indicates the presence of at least one cell carrying replication-competent HIV-1 virus. The concentration of viral RNA in culture supernatants was determined by the Amplicor method (Roche Diagnostics). Values are expressed in HIV-1 RNA copies/ml. The results show that chaetocin induces HIV-1 recovery (re-activation) in 6 of 7 cultures of patients (Table 2B).

In addition, BIX-01294 induces HIV-1 recovery in HLA $DR^-$ CD25 $CD69^-$ $CD4^+$ T cells from ART-treated HIV-1 positive individuals with undetectable viral load. Cultures of $2.5 \times 10^5$ HLA $DR^-$ CD 25 $CD69^-$ $CD4^+$ T cells were mock-treated or treated with BIX-01294. Six days after treatment, the concentration of viral RNA in culture supernatants was determined (Table 4).

Example 3

The Combined Treatment Chaetocin+Prostratin Synergistically Increases HIV-1 Transcription and Production in the Latently-infected Cells and in Patient's Cells FIG. 2 shows that the combined treatment chaetocin+ prostratin synergistically increases HIV-1 transcription in the latently-infected J-Lat 15.4 cell line. The J-Lat 15.4 cell line was mock-treated or treated as with chaetocin, prostratin or a combination of both drugs. Total RNA from these cells was extracted and reverse-transcribed using random primers. cDNAs were then used in a PCR reaction with primer pairs hybridizing either in TAR to quantify initiated transcripts or in Tat to quantify elongated transcripts. Results were normalized using β actin and are presented as histograms indicating the fold induction compared to mock-treated conditions. Moreover, the combinatory treatment including chaetocin and prostratin induce a higher viral production in some ex-vivo cultures of resting memory $CD4^+$ T cells from HIV-1-infected, cART-treated patients. Cultures of resting memory $CD4^+$ T cells were mock-treated or treated as indicated. Six days after treatment, the concentration of viral RNA in culture supernatants was measured (in copies/ml). The reactivated patient cultures were classified in relevant categories where HIV-1 recovery after the combined treatment presented a higher viral production than after the individual treatment (FIG. 3a).

Example 4

Effect of the Combined Treatment DNA Methylation Inhibitor 5-aza-CdR and the HDAC Inhibitor on HIV-1 Gene Expression FIG. 5 shows that cotreatment 5-aza-CdR+HDACI synergistically increases HIV-1 production and induces HIV-1 expression in a higher proportion of cells than the drugs alone in the latently-infected J-Lat 8.4 cell line. The J-Lat cell line harbor a full-length latent HIV-1 provirus containing GFP (Green Fluorescent Protein) in place of nef. The J-Lat 8.4 cell line was mock-treated or treated with 5-aza-CdR alone or in combination with the HDACIs. A. p24 production in cell supernatants was measured. The result obtained with mock-treated cells was arbitrarily set at a value of 1. B. Cells were fixed with paraformaldehyde and analyzed by flow cytometry to quantify the proportion of cells expressing GFP. Results (% of $GFP^+$ cells) are presented as histograms. C. The combined treatment 5-aza-CdR+SAHA or 5-aza-CdR+NaBut synergistically induces transcription from the HIV-1 5'LTR. The J-Lat 8.4 cell line was mock-treated or treated with 5-aza-CdR alone or in combination with SAHA or Nabut. Total RNA from these cells was extracted and reverse-transcribed using random primers. cDNAs were then used in a PCR reaction with primer pairs hybridizing either in TAR to quantify initiated transcripts or in Tat to quantify elongated transcripts. Results were normalized using β actin gene primers and are presented as histograms indicating the fold induction compared to mock-treated conditions.

The invention claimed is:

1. A method for treating an infection caused by HIV-1, HIV-2, HTLV-1 or HTLV-2 in a subject in need of such treatment, comprising administering to said subject a therapeutically effective amount of:
   a) 5-aza-2'-deoxycytidine (5-aza-CdR, decitabine), and
   b) a histone deacetylase inhibitor selected from the group consisting of: a hydroxamate, an aliphatic fatty acid, a benzamide, and a cyclic peptide,
   wherein the histone deacetylase inhibitor is administered after the administration of 5-aza-CdR.

2. The method according to claim 1, wherein said hydroxamate, aliphatic fatty acid, benzamide or cyclic peptide is selected from the group consisting of: TSA, suberoylanilide hydroxamic acid (SAHA), MS-275, M-Carboxycinnamic acid bishydroxamate, LAQ-824, belinostat (PXD-101), Panobinostat (LBH-589), a cinnamic hydroxamic acid analogue of M-carboxycinnamic acid bishydroxamate, IF2357, depsipeptide, apicidin, Romidepsin (FK-228), red FK, butyrate, phenylbutyrate, sodium butyrate (NaBut), valproic acid, pivaloyloxymethyl butyrate, etinostat (5 NOX-275), and MGCD0103.

3. The method according to claim 1, wherein said hydroxamate, aliphatic fatty acid, benzamide or cyclic peptide is panobinostat, belinostat, romidepsin, valproic acid, entinostat, apicidin, SAHA or NaBut.

4. A pharmaceutical composition or formulation comprising:
   a) 5-aza-2'-deoxycytidine (5-aza-CdR, decitabine),
   b) a histone deacetylase inhibitor selected from the group consisting of: a hydroxamate, an aliphatic fatty acid, a benzamide, and a cyclic peptide, and
   c) one or more solvents and/or one or more pharmaceutically acceptable carriers, wherein said 5-aza-2'-deoxycytidine is released from said composition or formulation prior to the release of said histone deacetylase inhibitor.

5. A pharmaceutical composition or formulation comprising a therapeutically effective amount of:
   a) 5-aza-2'-deoxycytidine (5-aza-CdR, decitabine),
   b) a histone deacetylase inhibitor selected from the group consisting of: a hydroxamate, an aliphatic fatty acid, a benzamide, and a cyclic peptide, and
   c) one or more solvents and/or one or more pharmaceutically acceptable carriers,
   wherein said composition is effective at treating an infection caused by HIV-1, HIV-2, HTLV-1 or HTLV-2, and wherein said 5-aza-2'-deoxycytidine is released from said composition or formulation prior to the release of said histone deacetylase inhibitor.

6. The pharmaceutical composition according to claim 4, wherein said hydroxamate, cyclic peptide, aliphatic acid, or benzamide is selected from the group consisting of TSA, SAHA, MS-275, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, depsipeptide, apicidin, Romidepsin (FK-228), red FK, butyrate, phenylbutyrate, sodium butyrate (NaBut), valproic acid, pivaloyloxymethyl butyrate, 5 NOX-275, and MGCD0103.

7. The pharmaceutical composition according to claim 4, wherein said hydroxamate or aliphatic fatty acid is SAHA or NaBut, respectively.

8. The method according to claim 1, wherein said disease or condition is a latent infection.

9. The method of claim 1, wherein the infection is caused by HIV-1 or HIV-2.

10. The pharmaceutical composition or formulation of claim 5, wherein the infection is caused by HIV-1 or HIV-2.

11. A method for treating an HIV-1 or an HIV-2 infection in a subject in need of such treatment, comprising administering to said subject a therapeutically effective amount of:
    a) 5-aza-2'-deoxycytidine (5-aza-CdR, decitabine), and
    b) a histone deacetylase inhibitor selected from the group consisting of: a hydroxamate, an aliphatic fatty acid, a benzamide, and a cyclic peptide,
    wherein the histone deacetylase inhibitor is administered after the administration of 5-aza-CdR.

12. The method according to claim 11, wherein said hydroxamate, aliphatic fatty acid, benzamide or cyclic peptide is selected from the group consisting of: TSA, suberoylanilide hydroxamic acid (SAHA), MS-275, M-Carboxycinnamic acid bishydroxamate, LAQ-824, belinostat (PXD-101), Panobinostat (LBH-589), a cinnamic hydroxamic acid analogue of M-carboxycinnamic acid bishydroxamate, IF2357, depsipeptide, apicidin, Romidepsin (FK-228), red FK, butyrate, phenylbutyrate, sodium butyrate (NaBut), valproic acid, pivaloyloxymethyl butyrate, etinostat (5 NOX-275), and MGCD0103.

13. The method according to claim 11, wherein said hydroxamate, aliphatic fatty acid, benzamide or cyclic peptide is panobinostat, belinostat, romidepsin, valproic acid, entinostat, apicidin, SAHA or NaBut.

14. The method of claim 13, wherein the infection is an HIV-1 infection.

* * * * *